United States Patent [19]

Wilson

[11] 4,215,441
[45] Aug. 5, 1980

[54] PROSTHETIC HIP

[75] Inventor: Michael T. Wilson, Concord, Calif.

[73] Assignee: Thomas Haslam, Houston, Tex.; a part interest

[21] Appl. No.: 11,127

[22] Filed: Feb. 12, 1979

[51] Int. Cl.² .......................... A61F 1/08; A61F 1/04
[52] U.S. Cl. ............................................. 3/15; 3/21; 3/27
[58] Field of Search ................. 3/15, 17 R, 21, 27, 3/2

[56] References Cited

U.S. PATENT DOCUMENTS

| 3,501,777 | 3/1970 | Degtyarev et al. | 3/15 |
| 3,863,274 | 2/1975 | Glabiszewski | 3/27 |
| 4,051,558 | 10/1977 | Vallotton | 3/15 X |

OTHER PUBLICATIONS

"The IPOS Hip Joint for Hip Disarticulation or Hemipelvectomy Prostheses," Hosmer Dorrance Corp., P.O. Box 37, Campbell, Calif., (4 pages) received Jun. 23, 1978, Group 330.

Primary Examiner—Ronald L. Frinks
Attorney, Agent, or Firm—Phillips, Moore, Weissenberger, Lempio & Majestic

[57] ABSTRACT

A prosthesis for replacement of a hip joint is flexion biased so that the prosthetic limb members affixed thereto are urged anteriorly of the body with the prosthetic foot off the ground. Thus, when the prosthetic hip joint is used with the weight activated knee joint, the flexion biasing provides swing phase motion to the leg from energy stored in the biasing member during the stance phase of that leg.

15 Claims, 10 Drawing Figures

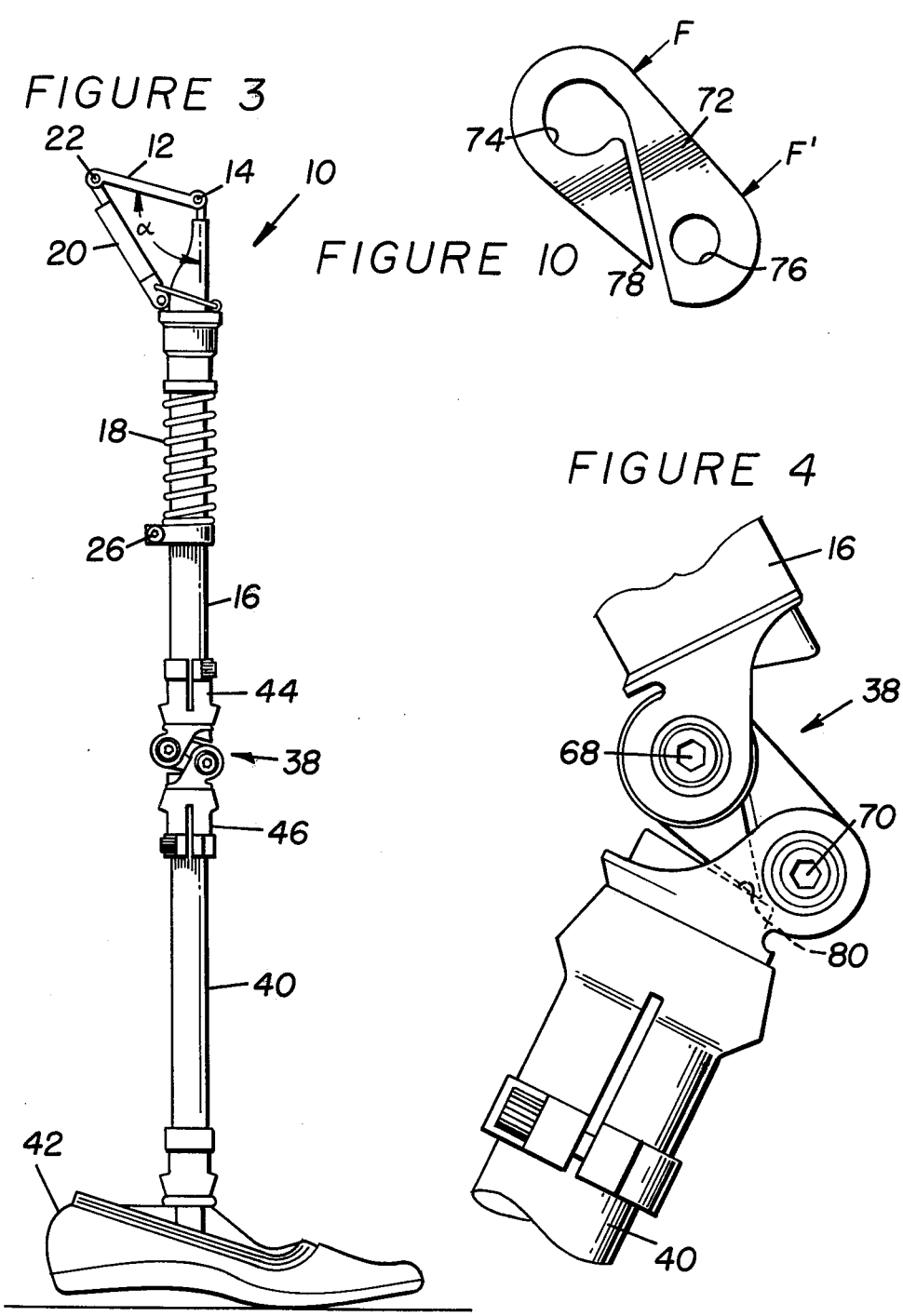

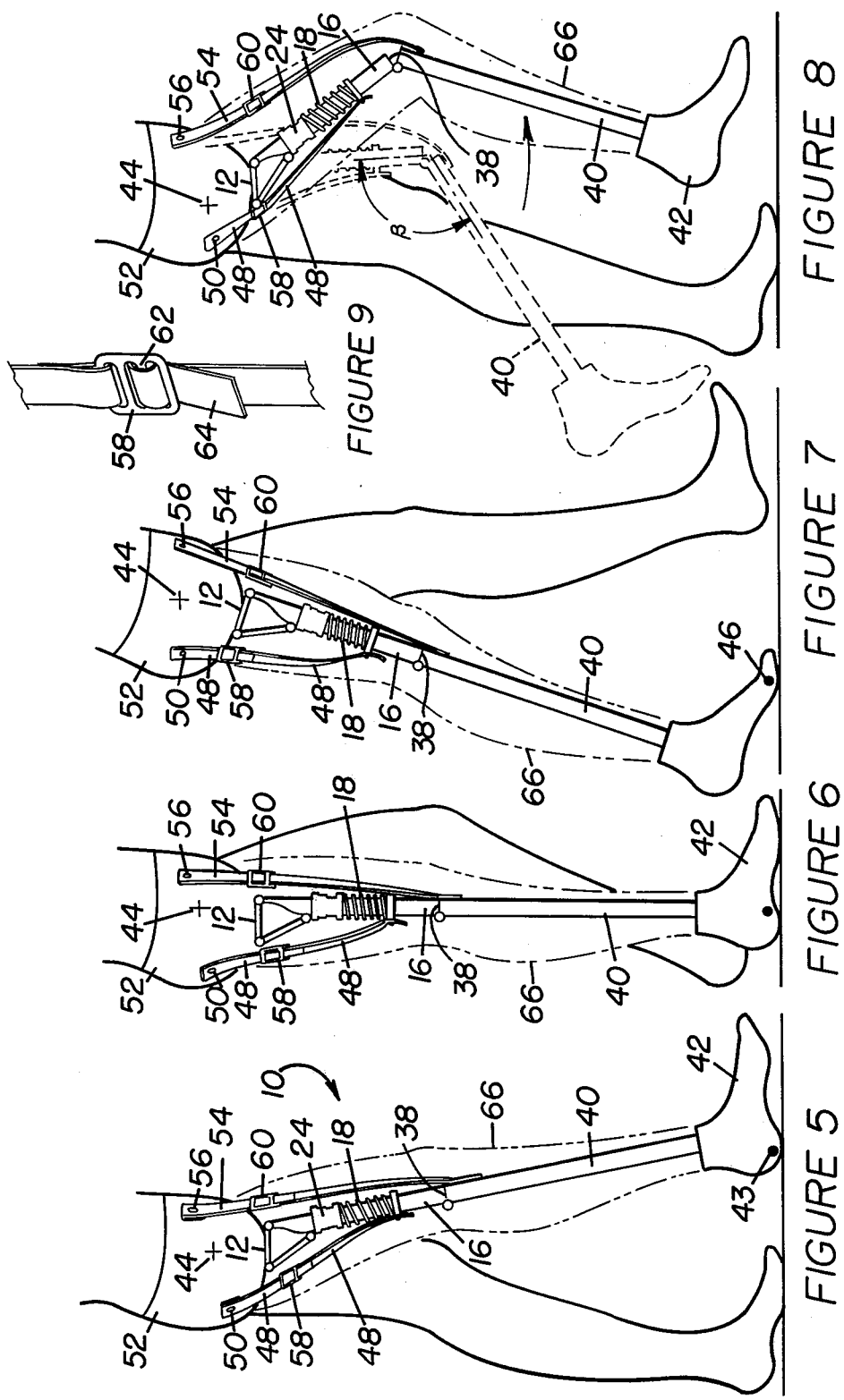

PROSTHETIC HIP

BACKGROUND OF THE INVENTION

This invention relates to a prosthetic device. Specifically it relates to a prosthetic hip joint for use with a prosthetic upper and lower limb to replace an entire lower limb and the associated hip joint.

Upon removal of a portion of the pelvis of a humam, replacement of the hip joint becomes a necessity if the patient is to resume walking. It is to be understood that removal of the upper and lower limb for medical reasons caused either by trauma or disease results in concurrent removal of the musculature of the leg. If there is a residual portion of the upper limb remaining the patient retains a degree of control over the swing of a prosthesis. However should it become necessary to remove the hip joint and a portion of the pelvis the patient has no muscular ability to swing an artificial limb and thus achieve any degree of ambulation without swinging his torso. Furthermore control of the knee is lost by loss of the muscle structure of the upper and lower limb.

If an operative knee joint is to be included in a prosthesis for a complete limb, articulation of that replacement knee joint is usually accomplished by the swing motion of the leg. Thus as the patient swings the residual upper limb forward the replacement knee may flex due to the inertia of the foot. When the residual limb is stopped anterior of the body the inertia of the lower limb now carries the lower limb forward thus extending the knee so that the entire prosthesis is in generally a straight line at the time heel contact occurs. If the amputee does not have a residual limb so that muscle structure does not remain to swing the residual limb and an associated prosthesis forward, either the body must be utilized to swing the prosthesis or some mechanical structure must accomplish the swing.

In existing prosthetic hip replacement structures for use with an artificial limb, the emphasis has been on biasing the artificial limb to remain in the frontal plane of the body. With this approach the amputee has a second burden placed on him in the event of a complete hip replacement. In addition to having to swing the prosthesis by body muscle, the amputee must also overcome the biasing of the prosthesis to remain in the frontal plane. Prostheses of this type have been necessitated generally because of the knee structure. Prosthetic knees, in the past, were not designed to shift from an unlocked (flexing) to a locked (extended) condition during walking by the patient. This limitation has recently been overcome by the introducton of a weight activated knee joint. This knee joint is available from the Otto Bock Company of West Germany and is designed such that upon heel contact of an associated prosthetic foot the force applied to the upper limb through the knee joint locks the knee. As the prosthesis passes through mid-stance the knee joint mechanically unlocks yet remains bimechanically locked to the point of heel-off at which time the knee is free to flex.

With the advent of this new knee joint, the knee joint limitation imposed upon a prosthetist in designing a full leg replacement including a hip joint is largely overcome. Specifically the prosthetist no longer has to worry about the knee flexing at heel contact. Nevertheless the prosthetic equipment manufacturers have continued to provide the extension biased hip joints (described above) which bias the prosthetic members to the frontal plane of the body. Tests with patients utilizing such structures indicate the energy requirements to operate extension biased hips and the associated lower limb were approximately twice the normal energy requirements.

It was with this background that the flexion biased prosthesis described herein was developed. Specifically the flexion biased prosthesis described herein overcomes the major drawback of the commonly used extension biased hip joint in its primary objective of reducing energy requirements to an amputee to a minimum level.

It is a further object of the present invention to provide a lightweight easily operable structure for complete lower limb replacement.

It is also an object of this invention to provide a prosthesis which may be adjusted by the user for different conditions. Other objects will become apparent from a study of the accompanying drawings and the following specification.

SUMMARY OF THE INVENTION

Specifically this invention relates to a flexion biased prosthesis which includes an upper limb pylon. A bearing plate is adapted for mounting on a hip socket with the bearing plate being pivotally affixed to the superior end of the upper limb pylon. Means are included for flexing the upper limb pylon relative the bearing plate so that with the bearing plate fixed to a hip socket the upper limb pylon is flexed forwardly of the frontal plane.

BRIEF DESCRIPTION OF THE DRAWINGS

FIG. 3 is an elevation view of a prosthetic limb including the flexion biased hip joint disclosed herein.

FIG. 4 is a detailed elevation view of a weight activated prosthetic knee for use with the flexion biased hip joint.

FIG. 5 is a side view of the prosthesis shown in FIG. 3 in use at heel contact.

FIG. 6 is the same prosthesis shown in FIG. 5 at mid-stance.

FIG. 7 is the same prosthesis shown in FIG. 6 at toe-off.

FIG. 8 is the prosthesis shown in FIG. 7 during swing phase.

FIG. 9 is an adjusting buckle for use with the restraining straps.

FIG. 10 is the locking wedge of the prosthetic knee shown in FIG. 4.

DETAILED DESCRIPTION OF THE PREFERRED EMBODIMENT

Figures 1, 2:
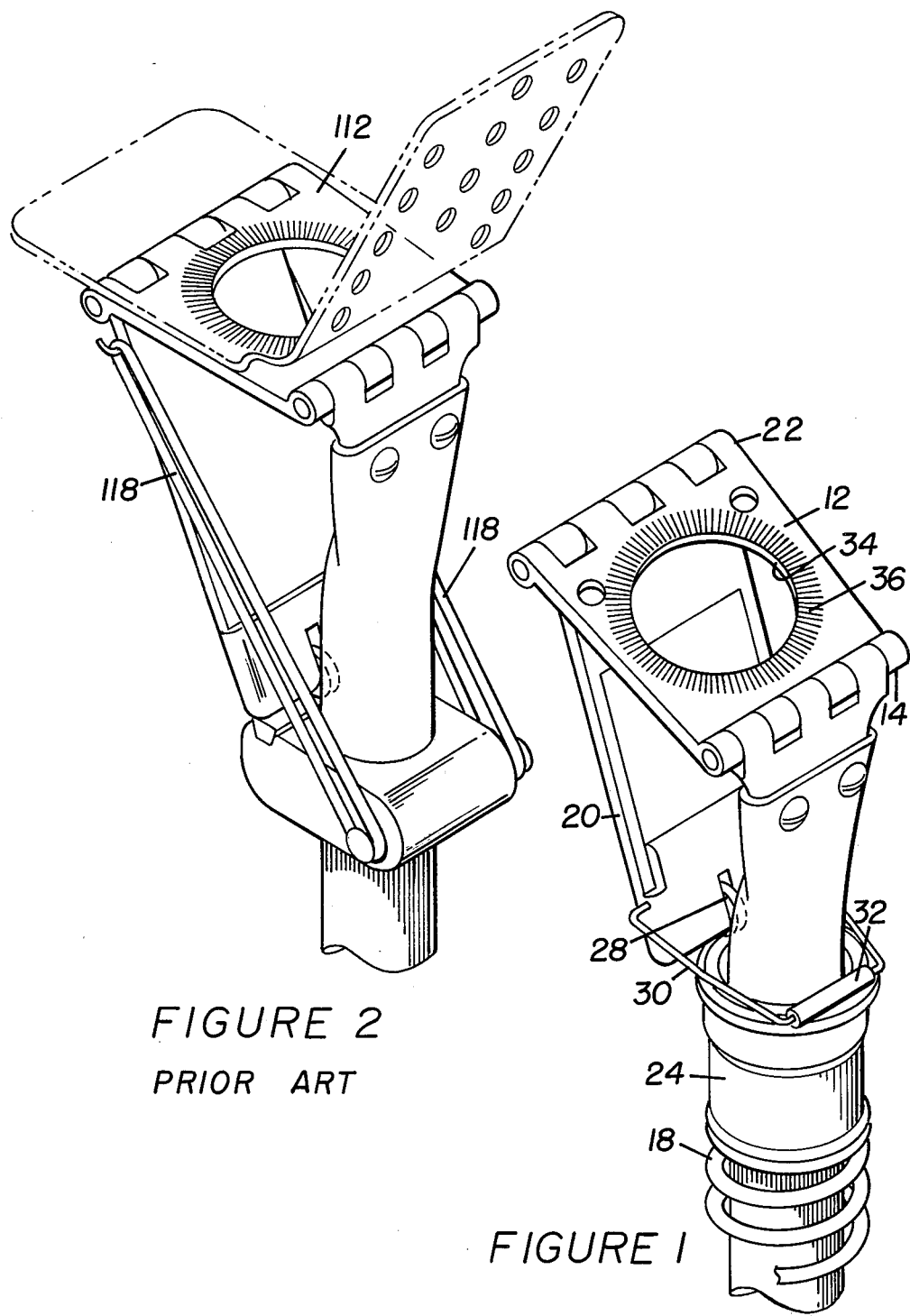
FIG. 1 is an axonometric projection of the flexion biased hip joint disclosed herein.
FIG. 2 is an axonometric projection of a prior art extension biased hip joint.

Referring to FIG. 3, a flexion biased prosthesis 10 is illustrated. Flexion biased prosthesis 10 includes a bearing plate 12 adapted for mounting on a hip socket 52 (see FIG. 5). Bearing plate 12 is pivotally affixed by a hinge 14 to an upper limb pylon 16. Means are provided for flexing the upper limb pylon 16 relative the bearing plate 12. These flexor means include a resilient compression member 18 and a rigid member 20 pivotally affixed to bearing plate 12 by hinge 22 or the like at the end of bearing plate 12 distal of upper limb pylon 16.

Rigid member 20 bears against a collar 24 slidably mounted about upper pylon 16 and in an abutting relation with the upper or superior end of resilient compression member 18. The lower or inferior end of resilient compression member 18 abuts an adjustable stop member 26 fixedly positionable on upper pylon 16.

Rigid member 20 may have formed therewith a roller 28 (see FIG. 1) which abuts upper pylon 16 and collar 24 to facilitate movement of rigid member 20 upwardly and downwardly relative upper pylon 16. Also associated with rigid member 20 is a bail or retainer 30 which includes a roller 32 on the cross member portion thereof (see FIG. 1). Retainer 30 acting in cooperation with roller 32 assists in retaining rigid member 20 in an abutting relation with upper pylon 16.

The upper surface of bearing plate 12 may include a bore 34 and a circular toothed surface 36 adapted specifically for mounting on hip socket 52.

Referring now to FIG. 3 and 4, the remaining portions of the flexion biased prosthesis will be discussed. Upper pylon 16 has affixed at the inferior end thereof a weight actuated knee 38 well known in the art and manufactured by the Otto Bock Company of West Germany. Other weight actuated knees would suffice for use with this invention. A brief description of weight actuated knee 38 is included in a later portion of this specification. Suffice it to say, at this point, that when weight is applied to this knee at heel contact, (see FIG. 5) so that the line joining the center of gravity 44 of the body and the point of contact 43 with the ground is behind the knee joint, the knee locks. As this line joining the center of gravity with the point of contact with the ground moves through the knee joint, the knee unlocks permitting free knee flexion as illustrated in FIG. 8 during swing phase.

Inferior of weight activated knee 38 is a lower pylon 40 and a prosthetic foot 42. Interconnection of these various elements inferior of upper pylon 16 is in a manner well known in the art and will not be further discussed here other than to say that rotation of each element about an axis perpendicular to the transverse plane may be accomplished by appropriate fastening means such as slotted sockets 44 and 46 respectfully joining upper pylon 16 with weight activated knee 38 and weight activated knee 38 with lower pylon 40. A similar arrangement may be provided between lower pylon 40 and foot 42.

Referring again to FIG. 3 it can be seen that resilient compression member 18 in this particular embodiment is a helical spring surrounding upper pylon 16. It should be understood that other resilient compression members may be substituted for the helical spring illustrated in FIG. 3. The purpose of the resilient compression member 18 is to cause an upward bias on rigid member 20 thus positioning bearing plate 12 at an obtuse angle $\alpha$ with upper limb pylon 16. With the bearing plate 12 biased to an obtuse angle and when bearing plate 12 is fixed to hip socket 52 shown schematically in FIG. 5 the upper limb pylon and the remaining portions of the flexion biased prosthesis are extended anteriorly of the frontal plane as indicated in FIG. 5. Ideally this angle is approximately 20° from the frontal plane so that angle $\alpha$ is approximately 110°. It should be understood that angles greater or less than 20° may be appropriate in particular situations. Angle $\alpha$ which is illustrated in FIG. 3 may be varied by adjustment of adjustable stop member 26 upwardly and downwardly on upper limb pylon 16. It is emphasized that angle $\alpha$, with bearing plate 12 fixed to socket 52 so that bearing plate 12 is parallel to the ground as shown in FIG. 3, should be obtuse. This obtuse angle will achieve the necessary extension anteriorly of the frontal plane again as shown in FIG. 5.

Restraining means are provided to prevent upper limb pylon 16 from swinging too far forwardly from the anterior plane. Accordingly a first restraining strap 48 is adapted for fixture at one end as at 50 to socket 52. Strap 48 is fixed at its other end to pylon 16 in the vicinity of stop member 26 or to stop member 26. Fixture point 50 is moved partially to the side of socket 52 so that when the patient is in a sitting position restraining strap 48, which is ideally of a resilient material, may slide around and permit the upper limb pylon to assume an angle of approximately 90° with the frontal plane of the body. Restraining strap 48 may be replaced by other restraining means such as a spring mechanism in rigid member 2. Restraining strap 48 is to inhibit rotation of the upper limb pylon 16 beyond a predetermined anterior angle of the upper limb during swing phase. This restriction has the beneficial effect of imparting the momentum of the resilient compression member 18 to the lower limb pylon 40.

A second strap 54 is affixed at is upper end to socket 52 at a point 56. Strap 54 is affixed at its other end at a point on the prosthesis below weight activated knee 38. Strap 54 also should be of a resilient material to permit a degree of extension. Strap 54 is adapted to prevent excessive flexion of knee 38 during the swing phase. This is particularly appropriate when the patient changes from a lightweight shoe to a heavy shoe. The heavy shoe, having additional inertia, will cause lower limb pylon 40 to flex excessively before commencing the swing forward. Strap 54 may be adjusted so that angle $\beta$ (see FIG. 8) between the upper and lower limb pylons does not become less than a predetermined amount, ideally approximately 120°.

Both strap 48 and strap 54 have adjusting buckles 58 and 60 respectively. These buckles may be of a type similar to that shown in FIG. 9 which are well known in the art and which include a sliding toggle 62 about which bitter end 64 passes. Tension on bitter end 64 will shorten the effective length of strap 64 also in a manner well known in the art and further discussion is not necessary. It is important that buckles 58 and 60 with the appropriate bitter ends 64 of each strap are outside of the cosmetic portion 66 of the prosthesis which is molded about the mechanical portions. By positioning the buckles and bitter ends exterior of the cosmetic portion the patient may adjust the length of these restraining straps to compensate for either a slower or faster cadence or more importantly a different shoe weight. Again it is important to understand that other resilient restraining members may replace strap 48 and strap 54 as long as the replacements serve the purpose set forth above.

The prior art device illustrated in FIG. 2 has a similar bearing plate 112 but is biased by resilient members 118 to an extension position. Therefore utilizing the prior art device illustrated in FIG. 2, the prosthesis will seek the relative position shown in FIG. 6, that is a vertical orientation, in the frontal plane. In order to shift the prosthesis out of the frontal plane a patient must contract the muscles of the stomach to whip or swing the prosthesis forward by shifting the entire torso. As indicated in the background portion of this specification such efforts require about twice the normal effort to walk with two sound limbs.

Operation of the described embodiment is as follows. Referring to FIG. 5 the prosthesis is shown in an unloaded state at the point of heel contact. It should be understood that knee joint 38 is shown fully extended. Normally should a patient stand up the upper limb 16 will extend anteriorly as shown in FIG. 5. Without further effort by the patient the weight activated knee 38 would flex so that the lower limb pylon 40 would be approximately vertical due to the weight of foot 42 while the upper limb is extended forward of the body. However when a patient initially stands he may bend at the waist so the prosthesis is straight. Weight then may be placed on prosthesis 10 with the leg fully extended thus locking weight actuated knee 38. The patient would then stand erect. As weight is placed on the prosthesis the obtuse angle α is decreased until bearing plate 12 is substantially horizontal as shown in FIG. 7. At this time resilient compression member 18 is fully loaded by action of rigid member 20 forcing collar 24 downwardly against the bias of resilient compression member 18. As previously indicated when the center of gravity 44 of the amputee is immediately above or forward of weight actuated knee 38, the knee mechanically unlocks and biomechanically locks. This position is known as mid-stance. As the patient moves forward from mid-stance to toe-off, as shown in FIG. 7, the bearing plate 12 remains substantially at right angles to upper pylon 16 with resilient compression member 18 remaining fully loaded. It should be noted that the line connecting center of gravity 44 and the ground contact point 46 as illustrated in FIG. 7 is now well forward of weight actuated knee 38 so that weight actuated knee 38 is no longer mechanically locked, but is biomechanically locked.

As the toe leaves the ground in FIG. 7 resilient compression member 18 extends forcing collar 24 upwardly on upper limb pylon 16. The motion of collar 24 acts on rigid member 20 thus restoring orientation of bearing plate 12 relative upper limb pylon 16, that is angle α is again an obtuse angle. As this occurs upper limb pylon 16 swings forwardly or anteriorly of frontal plane of the amputee. Such swinging motion of upper limb pylon 16 initially causes weight actuated knee 38 to flex. As upper limb pylon 16 reaches the desired forward angular relationship with the patient, the resilient compression member 18 is fully unloaded and the forward motion of upper limb pylon 16 is checked by strap 48. Similarly when angle β reaches the desired predetermined value (about 120°) strap 54 checks further flexion and lower limb pylon starts to swing forward. The motion imparted to upper limb pylon 16 by the unloading of resilient compression member 18 and translated to the lower limb pylon 40 is indicated in Fig. 8. Lower limb pylon 40 follows through in the swing phase of the leg eventually achieving the straight relationship shown in FIG. 5. Ideally the patient will place his prosthetic foot 42 in heel contact with the ground concurrent with weight actuated knee 38 achieving full extension. Operation of this flexion biased prosthesis requires about 50% more effort than is required of a person with two sound limbs.

During fitting, adjustable stop member 26 is positioned on upper pylon 16 so that flexion of the hip joint is about 20°. Resilient compression member 16 may be chosen with a spring constant commensurate with the weight of the patient. Final adjustments and adjustments by the patient may be made by lengthening or shortening straps 48 and 54. Furthermore the resiliency of these two members may be varied to fit varying conditions should such a course of action be necessary.

It is appropriate to explain the operation of the weight activated knee 38 although this knee is available through the Otto Bock Company of West Germany. Weight activated knee 38 is fixed to the upper pylon 16 by appropriate fastening means and to the lower pylon 40 again by appropriate fastening means. A first hinge 68 provides the articulation of the knee itself. A second hinge 70 provides the locking feature. Hinged at 70 is the wedge shaped locking member 72. As can be seen, hinge pin 68 passes through a bore 74 while the hinge pin of hinge 70 passes through a second bore 76 (see FIG. 10). When a force is applied as at F' in FIG. 10, the locking member 72 is compressed about the hinge pin of hinge 68 due to the tongue 78 of locking member 72 bearing against the fixed portion 80 of the inferior part of weight activated knee 38. As the prosthesis passes mid-stance the force F' moves forward to a position approximately as indicated at F' of FIG. 10 so that weight is taken from tongue 78 unlocking member 72 so that the weight activated knee 38 is free to articulate again.

Although this invention has been described in relation to a particular embodiment it is to be understood that variations and changes can be made thereto without departing from the spirit and content of this invention. Specifically it is to be understood that where resilient members are described as specific types other types of resilient members or a comparable substitute may be used.

What is claimed is:

1. A flexion biased prosthesis comprising:
an upper limb pylon;
a bearing plate adapted for mounting on a hip socket; said bearing plate pivotally affixed to the superior end of said upper limb pylon;
flexor means for flexing said upper limb pylon relative said bearing plate whereby with said bearing plate fixed to a hip socket said upper limb pylon is flexed forwardly of the frontal plane.

2. The flexion biased prosthesis of claim 1 further comprising a weight actuated prosthetic knee joint affixed to the inferior end of the upper limb pylon.

3. The flexion biased prosthesis of claim 1 wherein the bearing plate extends outwardly and rearwardly of the upper limb pylon.

4. The flexion biased prosthesis of claim 3 wherein the flexor means comprises a resilient compression member.

5. The flexion biased prosthesis of claim 4 wherein the flexor means further comprises a rigid member affixed at one end to the end of the bearing plate distal of the upper limb pylon, said rigid member associated at its other end with the resilient compression member.

6. The flexion biased prosthesis of claim 5 wherein the resilient compression member comprises a helical spring disposed about the upper limb pylon, said prosthesis further comprising a first collar adjustably affixed to the upper limb pylon said helical spring in abutting engagement with said collar and extending along said upper limb pylon in a superior direction from said collar.

7. The flexion biased prosthesis of claim 6 further comprising a second collar slidably disposed about the upper limb pylon between the helical spring and the bearing plate.

8. The flexion biased prosthesis of claim 7 wherein the other opposite end of the rigid member engages the superior end of the second collar.

9. The flexion biased prosthesis of claim 8 further comprising a retaining bail affixed to the rigid member and surrounding the upper limb pylon.

10. The flexion biased prosthesis of claim 9 further comprising a weight actuated prosthetic knee joint affixed to the inferior end of the upper limb pylon.

11. The flexion biased prosthesis of claim 2 or claim 10 further comprising a lower limb pylon and a prosthetic foot, said lower limb pylon affixed to the inferior side of the weight actuated prosthetic knee, said prosthetic foot affixed to the inferior end of said lower limb pylon.

12. The flexion biased prosthesis of claim 1 or claim 10 further comprising restraining means for inhibiting pivotal movement of said upper limb pylon forwardly from the frontal plane.

13. The flexion biased prosthesis of claim 2 or claim 10 further comprising second restraining means for inhibiting flexion of the weight activated prosthetic knee.

14. A flexion biased prosthesis comprising:
a hip socket;
an upper limb pylon;
a bearing plate affixed to said hip socket;
a hinge pivotally affixing said upper limb to said bearing plate;
flexor means for flexing said upper limb pylon relative said bearing plate forward of the frontal plane of said hip socket.

15. The flexion biased prosthesis of claim 14 further comprising a weight actuated prosthetic knee joint affixed to the inferior end of the upper limb pylon.

* * * * *